United States Patent
Hua et al.

(10) Patent No.: US 8,329,222 B1
(45) Date of Patent: Dec. 11, 2012

(54) MAGNETIC NANOMEDICINE FOR TUMOR SUPPRESSION AND THERAPY

(75) Inventors: Mu-Yi Hua, Tao-Yuan (TW); Hong-Wei Yang, Tao-Yuan (TW); Cheng-Keng Chuang, Guishan Township, Taoyuan County (TW); See-Tong Pang, Taipei (TW); Rung-Ywan Tsai, Kaohsiung (TW); Kun-Lung Chuang, Taipei (TW)

(73) Assignee: Chang Gung University, Tao-Yuan (TW)

( * ) Notice: Subject to any disclaimer, the term of this patent is extended or adjusted under 35 U.S.C. 154(b) by 0 days.

(21) Appl. No.: 13/166,450

(22) Filed: Jun. 22, 2011

(51) Int. Cl.
*A61K 9/14* (2006.01)
*A61K 9/16* (2006.01)

(52) U.S. Cl. .................. 424/489; 424/490; 424/491

(58) Field of Classification Search .............. None
See application file for complete search history.

(56) References Cited

U.S. PATENT DOCUMENTS 7,906,376 B2 * 3/2011 Swaminathan ............. 438/122

OTHER PUBLICATIONS

Yang et al., "A new magnetic nanomedicine enhances the therapy efficiency for bladder cancer MGH-U1 cells," TechConnect World 2010 Conference and Expo, Jun. 22, 2010, pp. 103 and TU40.507.

* cited by examiner

*Primary Examiner* — Susan Tran
(74) *Attorney, Agent, or Firm* — Muncy, Geissler, Olds & Lowe, PLLC

(57) ABSTRACT

A magnetic nanomedicine for tumor suppression and therapy, comprising: a core, made of magnetic nanoparticles; a shell, encapsulating said core and is made of carboxylated polyaniline (SPAnH); and a tumor suppression medicine Epirubicin (EPI) or Doxorubicin (DOX) covalently bonded onto said shell. Said magnetic nanomedicine is capable of improving its thermal stability, and it can be dissolved uniformly in water, plus its superparamagnetic property, thus it can be guided by an outside magnetic field to concentrate to the site of tumor distribution to increase the local medicine concentration and enhance therapy effect.

5 Claims, 14 Drawing Sheets
(12 of 14 Drawing Sheet(s) Filed in Color)

MAGNETIC NANOMEDICINE FOR TUMOR SUPPRESSION AND THERAPY

BACKGROUND OF THE INVENTION

1. Field of the Invention

The present invention relates to a magnetic nanomedicine for tumor suppression and therapy, and in particular to a magnetic nanomedicine for tumor suppression and therapy, that can be implemented without the need of surgical operation, and that is also capable of increasing local medicine concentration by means of a magnetic field.

2. The Prior Arts

Presently, Epirubicin (EPI) is widely utilized in therapy of several cancer diseases, however, since it is strongly toxic to the heart, its dosage applied and its therapy effectiveness are rather limited. Presently, most of the carrier used to carry EPI is provided by polymer nano-particles, polymer vesicles and liposome of nano-structure. Though it has the advantages of avoiding being decomposed quickly in human body, and capable of being released gradually and slowly, hereby prolonging its circulation time in the body, yet its medicine encapsulation rate is restricted due to the particle size of the carrier, and its medicine releasing speed can not be precisely controlled, also its particle size is overly large (about 150-300 nm), thus it can not be concentrated in large quantity around the area of tumor, hereby causing serious side-effects to other organs of the human body. Therefore, the present invention provides a simplified manufacturing process to produce a new type of magnetic nano-medicine (EPI/SPAnH/MNPs, DOX/SPAnH/MNPs), that can be guided and concentrated to the tumor area by an external magnetic field without the need of a surgical operation, thus increasing local medicine concentration and effectiveness of therapy, and avoiding being toxic to the heart and causing side effects to the entire body due to over dosage.

In addition, presently, since the medicine of the prior art for treating malignant tumor, such as Epirubicin (EPI) is toxic to the heart, therefore, how to make use of a medicine delivery system to slow down the releasing speed of medicine in human body, and reducing its side-effects to various organs, such as heart, is an important task that has to be solved urgently in this field.

Therefore, presently, the design and performance of the magnetic nanomedicine of the prior art is not quite satisfactory, and it has much room for improvements.

SUMMARY OF THE INVENTION

In view of the problems and shortcomings of the prior art, such as the damages caused by medicine carrier in medicine releasing process to the human body, and the side effects incurred in treating tumor, the present invention provides a magnetic nanomedicine for tumor suppression and therapy.

The present invention provides a magnetic nanomedicine, having the advantages of free of toxic chemicals such as surfactants, dispersing agents and crosslinking agents, and it can be applied and put into human body without the need of a surgical operation, while raising its thermal stability and reducing the side effects of biological rejection; and it can be guided to the area of tumor cells distribution by an external magnetic field, in achieving the enhanced local therapy.

In order to achieve the above mentioned objective, the magnetic nanomedicine for tumor suppression and therapy of the present invention comprises: a core, made of magnetic particles of diameter less than 10 nm; a shell, encapsulating the core and is made of carboxylated polyaniline (SPAnH); and a tumor suppression and therapy medicine covalently bonded onto the shell. The present invention utilizes Epirubicin (EPI), Doxorubicin (DOX) or derivatives for tumor suppression and therapy, such that the magnetic nanomedicine thus formed is referred to as EPI/SPAnH/MNPs, or DOX/SPAnH/MNPs), The magnetic nanomedicine of the present invention is capable of improving its thermal stability over the conventional tumor therapy medicine, and it can be dissolved uniformly in water, plus its superparamagnetic property, thus it can be guided by an external magnetic field to concentrate into a specific area to increase the local medicine concentration. In-vitro cytotoxicity test shows that, in comparing pure EPI with magnetic nanomedicine (EPI/SPAnH/MNPs, and DOX/SPAnH/MNPs) having concentrations of 10 μM and an applied magnetic field of 800 Gauss, the killing rates of bladder tumor cell (MGH-U1) are increased 20.4% and 22.6% respectively, and that indicates that the magnetic nanomedicine of the present invention has a great economic advantage.

Further scope of the applicability of the present invention will become apparent from the detailed descriptions given hereinafter. However, it should be understood that the detailed descriptions and specific examples, while indicating preferred embodiments of the present invention, are given by way of illustration only, since various changes and modifications within the spirit and scope of the present invention will become apparent to those skilled in the art from this detailed descriptions.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The related drawings in connection with the detailed descriptions of the present invention to be made later are described briefly as follows, in which.

(A) Phase difference electronic microscopic photos of bladder tumor cell MGH-U1; (B) fluorescent electronic microscopic photos of living cells; and (C) fluorescent electronic microscopic photos of cell dyed. with Cy5.

Figure 11:
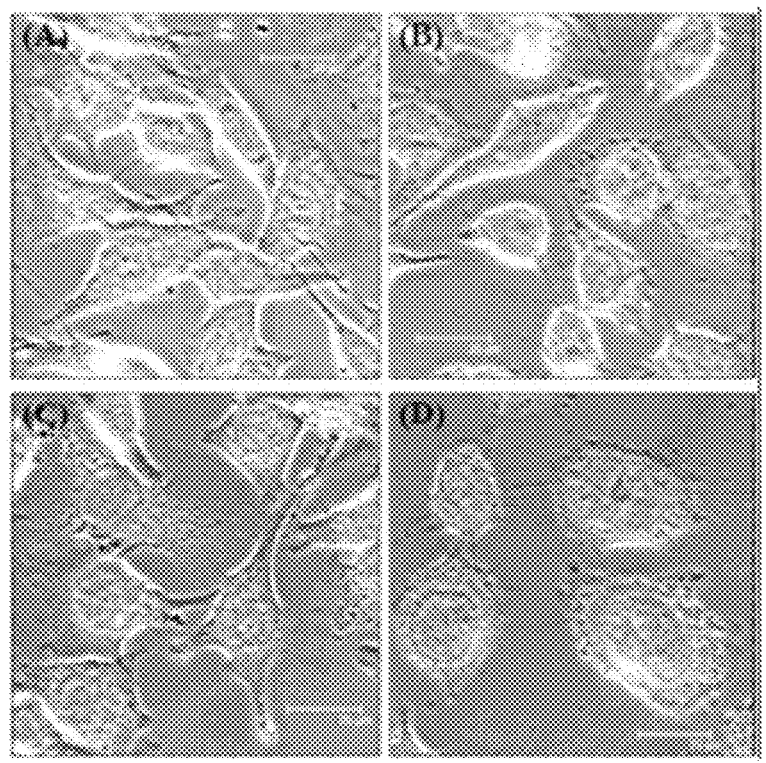

FIG. 11 includes electronic microscopic photos of bladder tumor cell MGH-U1: (A) fluorescent photos of bladder tumor cell MGH-U1 cultivated and reacted 4hours with Epirubicin. (EP1); (B) fluorescent photos of bladder tumor cell MGH-U1 cultivated and reacted 4 hours with EPI/SPAnH/MNPs magnetic manomedicine of the present invention; (C) fluorescent photos of bladder tumor cell MGH-U1 cultivated and reacted 4 hours with Doxorubicin (DOX); and (D) fluorescent photos of bladder tumor cell MGH-U1 cultivated and reacted 4 hours with DOX/ISPAnH/MNPs magnetic manomedicine of the present invention.

DETAILED DESCRIPTION OF THE PREFERRED EMBODIMENT

The purpose, construction, features, functions and advantages of the present invention can be appreciated and understood more thoroughly through the following detailed description with reference to the attached drawings.

Figure 9:
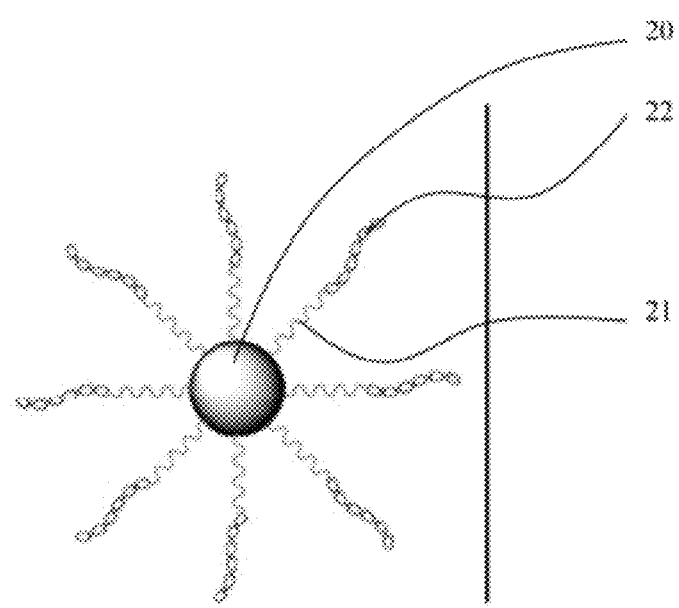
FIG. 9 is a schematic diagram of a magnetic nanomedicine according to the present invention.
Figure 10:
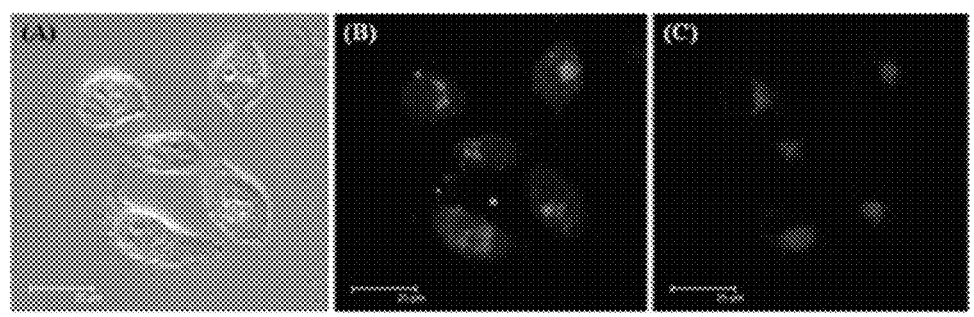
FIG. 10 includes electronic microscopic photos of bladder tumor cell MGH-U1.

The present invention provides a magnetic nano-medicine for tumor suppression and therapy. Refer to FIG. 9 for a schematic diagram of the structure of a magnetic nanomedicine for tumor suppression and therapy according to the present invention. As shown in FIG. 9, the particle diameter of the magnetic nanomedicine of the present invention is between 25 to 50 nm, and the structure of the magnetic nanomedicine comprises a core 20, a shell 21, and a tumor suppression medicine 22. Wherein, the core 20 is composed of magnetic nanoparticles of diameter less than 10 nm; the shell 21 encapsulates outside the core 20; the tumor suppression medicine 22 such as Epirubicin (EPI) and derivatives thereof, or Doxorubicin (DOX) and derivatives thereof, is covalently bonded onto the shell 21 under proper temperature, such as 20 to 25° C.

In the description mentioned above, the magnetic nanoparticles are selected from a group consisting of $Fe_3O_4$, $Fe_2O_3$, or Ni. The shell 21 is composed of carboxylated polyaniline (SPAnH), having the following formula:

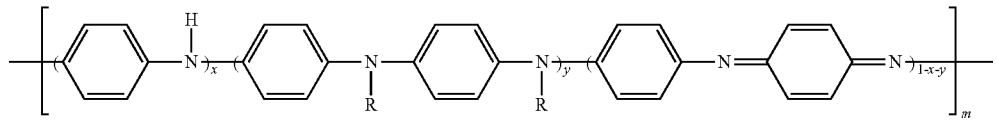

wherein, R is selected from a group consisting of the following functional groups: —H, —$COR_1COO^-$, —$COR_1COOH$, —$COR_1COOLi$, —$COR_1COONa$, —$COR_1COOK$, —$COR_1COONH_4^+$, $COR_1CONH_2$, —$R_1COO^-$, —$R_1COOH$, —$R_1COOLi$, —$R_1COONa$, —$R_1COOK$, —$R_1COONH_4^+$, and —$R_1CONH_2$; and R1 is selected from a group of compounds consisting of: alkane group and vinyl group composed of 2 to 4 carbon atoms.

In order to explain the various characteristics of the magnetic nanomedicine for tumor suppression and therapy of the present invention, various embodiments are described as follows:

Embodiment 1

Method of Preparing Magnetic Nanoparticles (MNPs) of Magnetic Nanomedicine of the Present Invention Preparation of MNPs: utilize a co-deposition method to prepare magnetic nanoparticles $Fe_3O_4$ (MNPs)

Firstly, add 0.7 gram of $FeCl_3$ (concentration $4.32 \times 10^{-3}$ mole), 1.07 gram of $FeCl_2.4H_2O$ (concentration $6.48 \times 10^{-3}$ mole), and 400 mL of double distilled water into a three-neck bottle, and stir it with a magnet in a nitrogen environment for 5 minutes, so as to make $FeCl_3$ and $FeCl_2.4H_2O$ fully dissolve into water; then add 20 mL NaOH aqueous solution of concentration 0.864 N into the three-neck bottle, and then heat it to a temperature of 80° C. to produce an aqueous solution containing MNPs.

Separating MNPs: after cooling down the aqueous solution containing MNPs, agitate it in an ultrasonic agitator to make the MNPs distributed uniformly in the aqueous solution; then pour the aqueous solution containing MNPs into a separating funnel, and place a strong magnet outside the funnel to attract MNPs, hereby allowing the aqueous solution to flow away from the bottom of the separating funnel, thus separating MNPs from the aqueous solution. Finally, add double distilled water to flush MNPs several times, until the aqueous solution flowing away from the bottom of the funnel is neutralized and colorless, with the particle size of about 8 nm.

Figure 2:
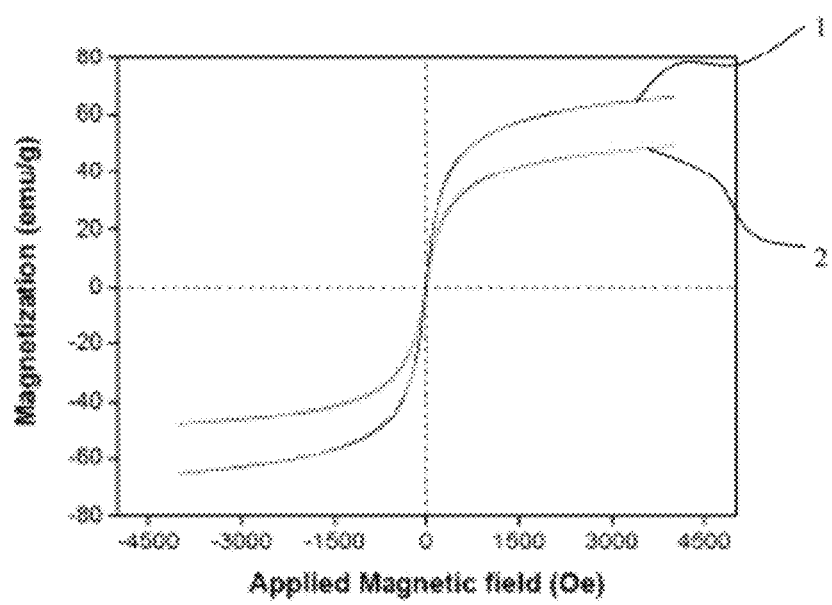
FIG. 2 is a magnetic hysteria curve for magnetic nanoparticle and magnetic nanoparticle of a shell encapsulated with carboxylated polyaniline (SPAnH) according to the present invention.

Refer to FIG. 2 for a magnetic hysteresis curve for magnetic nanoparticle and magnetic nanoparticle having encapsulated shell of carboxylated polyaniline (SPAnH) according to the present invention, and that shows the magnetization of MNPs as measured by a Superconducting Quantum Interference Device (SQUID). From FIG. 2, it can be known that, the saturation magnetization of MNPs is found to be 66.2 emu/g, which increases with the increase of the magnetic field, and the magnetization curve passes through the origin, such that the MNPs having the characteristic of superparamagnetism.

Figure 4:
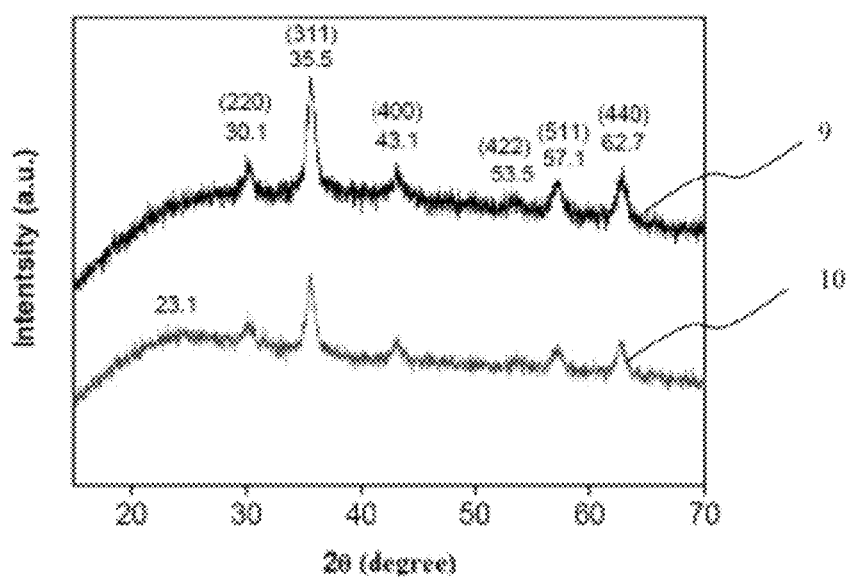
FIG. 4 is an X-ray diffraction analysis diagram of magnetic nanoparticle, and SPAnH/MNPs magnetic nanocomposite detected and taken in room temperature according to the present invention.

From the infrared spectrum of MNPs it can be known that, when the wave number is at 586⁻¹, the stretching vibrations of bonding between Fe and O atoms (Fe—O) in MNPs will appear. Furthermore, as shown in FIG. 4, it can be known the MNPs of the X-ray diffraction spectrum are $Fe_3O_4$.

Embodiment 2

Method of Producing a SPAnH/MNPs Magnetic Nanocomposite

Firstly, mix 2 mL of MNPs aqueous solution having concentration of 10 mg/mL, and 0.5 mL of SPAnNa (poly[aniline-co-sodium N-(1-one-butyric acid)aniline]) aqueous solution having concentration of 4.9 mg/mL uniformly into a mix solution, and put this mixed solution into an ultrasonic agitator to make its contents mix uniformly, then drop in HCl of concentration of 0.5 M. In an acidic environment, SPAnNa aggregates to form SPAnH, and the SPAnH envelops MNPs to form a e SPAnH/MNPs magnetic nanocomposite with the core being MNPs, and with the shell being SPAnH. Next, separate the SPAnH/MNPs magnetic nanocomposite from the solution, and disperse it in double distilled water, hereby forming a SPAnH/MNPs magnetic nanocomposite in aqueous solution.

Figure 1A:
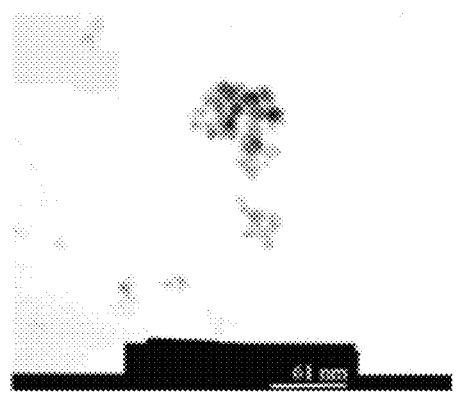
FIG. 1(A) is a transmission electronic microscopic photo of magnetic nanocomposite of magnetic nanoparticles of a shell encapsulated with carboxylated polyaniline (SPAnH)

The observation result of SPAnH/MNPs magnetic nanocomposite using a transmission electronic microscope is as shown in FIG. 1(A), wherein it shows that the diameter of SPAnH/MNPs magnetic nanocomposite particle is 17 nm. In FIG. 3 is shown infrared spectrum of SPAnH/MNPs magnetic nanocomposite, wherein, an Fe—O ($v_{Fe-O}$) stretching vibration appearing at 582 cm⁻¹; a saturation-symmetric stretching vibration and a saturation-asymmetric stretching vibration of C—H ($v_{C-H}$) appearing respectively at 2844 cm⁻¹ and 2927 cm⁻¹; and a C=O ($v_{C=O}$) stretching vibration and an O—H ($v_{O-H}$) stretching vibration of functional group —COOH appearing respectively at 1707 cm⁻¹ and 3410 cm⁻¹. The stretching vibrations of bonds mentioned above indicate MNPs are indeed enveloped by a layer of SPAnH.

Refer again to FIG. 2, which shows the magnetization of SPAnH/MNPs magnetic nanocomposite as measured by a SQUID, wherein, it can be known that the saturation magnetization of SPAnH/MNPs magnetic nanocomposite is 47.0 emu/g, and having the characteristic of superparamagnetism.

As shown in FIG. 4, from the X-ray diffraction spectrum of SPAnH/MNPs magnetic nanocomposite, it can be known that, its core is indeed made of $Fe_3O_4$.

Embodiment 3

Figure 5:
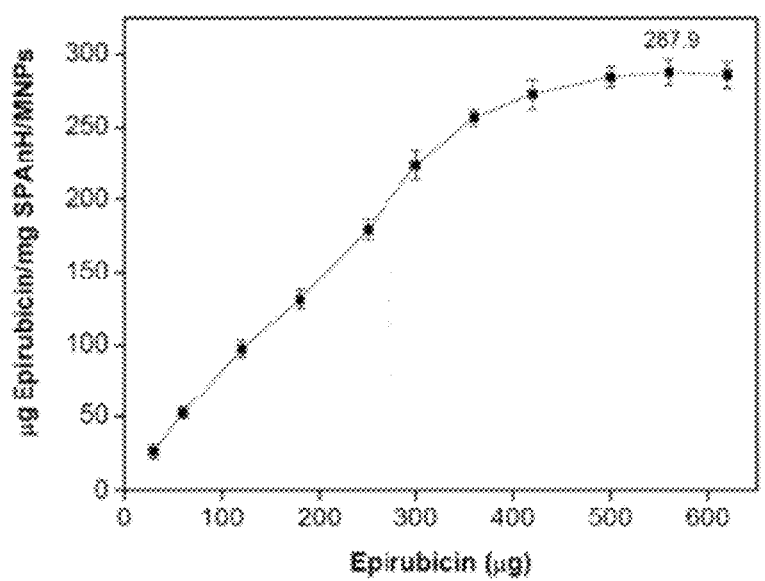
FIG. 5 is a bonding efficiency curve for bonding EPI of various concentrations onto SPAnH/MNPs magnetic nanocomposite according to the present invention.

Efficiency Of Preparing Epi/SPAnH/MNPs Magnetic Nanomedicine by Making Epirubicin (EPI) of Various Concentrations to React with SPAnH/MNPs Magnetic Nanocomposite, and the Maximum Medicine Bonding Efficiency Dissolve 24 mg of EDC (1-ethyl-3-3-(dimethylaminepropyl) carbodiimidehydro chloride) and 27 mg of sulfo-NHS (N-hydroxysulfosuccinimide sodium salt) in 0.5 M MES buffer (2-Morpholinoethanesulfonic acid, pH=6.3) to form a mixed reaction solution. Next, take 02.mL of the mixed reaction solution to react with 0.2 mL of SPAnH/MNPs magnetic nanocomposite solution for 30 minutes, and then flush the product with the MES buffer. Then, add 30 μg, 120 μg, 360 μg, or 560 μg of Epirubicin (EPI) medicine and perform medicine bonding reaction in temperature 20 to 25° C., to form EPI/SPAnH/MNPs magnetic nanomedicine, with its structure as shown in FIG. 9. Subsequently, flush off free EPI several times with de-ionized water. Then, determine the quantity of the flushed-off free EPI with HPLC (High Performance Liquid Chromatography), under the conditions of using a solution of alcohol/methanol/water (volume/volume/volume) 15/35/50, a flow rate of 1.5 mL/min and a detecting wavelength 256 nm. Work out the quantity of EPI bonded to SPAnH/MNPs magnetic nanocomposite from the quantity of the free EPI. Refer to FIG. 5, which shows that after SPAnH/MNPs magnetic nanocomposite reacts with 30 μg, 120 μg, 360 μg, or 560 μg of Epirubicin (EPI), the amount of EPI bonded onto each mg of SPAnH/MNPs magnetic nanocomposite are 26.4 μg, 97.4 μg, 257.1 μg, or 287.9 μg respectively, such that their medicine bonding efficiencies are 88%, 81%, 71%, 51% respectively. Therefore, it can be known that, when 560 μg of Epirubicin (EPI) is added, the maximum amount of EPI that can be bonded onto SPAnH/MNPs magnetic nanocomposite.

Figure 3A:
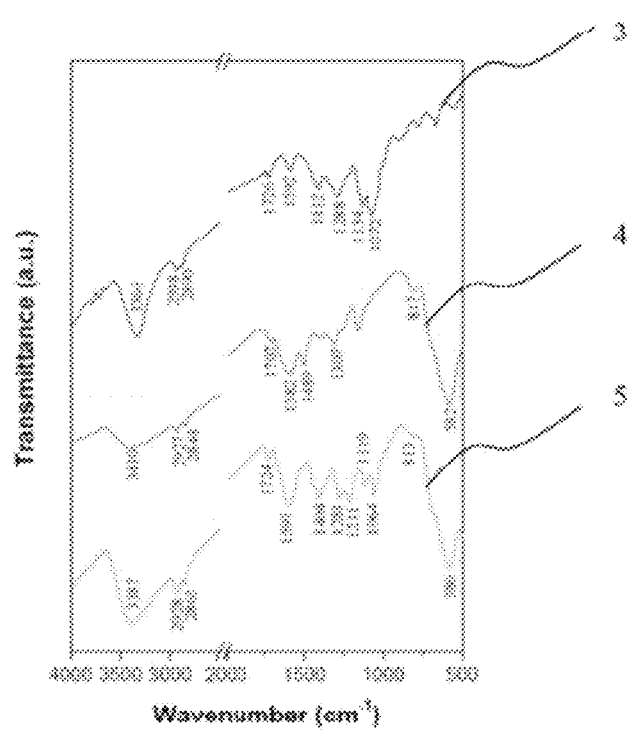
FIG. 3(A) is an infrared spectrum analysis diagram of Epirubicin (EPI), SPAnH/MNPs magnetic nanocomposite, and EPI/SPAnH/MNPs magnetic nanomedicine detected and taken in room temperature according to the present invention.

Refer to FIG. 3A for infrared spectrum of EPI/SPAnH/MNPs magnetic nanomedicine. In this spectrum, there is a Fe—O ($v_{Fe-O}$) stretching vibration appearing at 586 cm⁻¹, a saturation-symmetric stretching vibration and a saturation-asymmetric stretching vibration of C—H ($v_{C-H}$) appearing respectively at 2844 and 2927 cm⁻¹; C=O ($v_{C=O}$) stretching vibration of cyclopentanone appearing at 1724 cm⁻¹; C—O—C ($v_{C-O-C}$) stretching vibration appearing at 1119 cm⁻¹; and C=O ($v_{C=O}$) stretching vibration appearing at 1064 cm⁻¹, thus it indicates there are indeed EPI bonded onto the SPAnH/MNPs magnetic nanocomposite.

Embodiment 4

Figure 6:
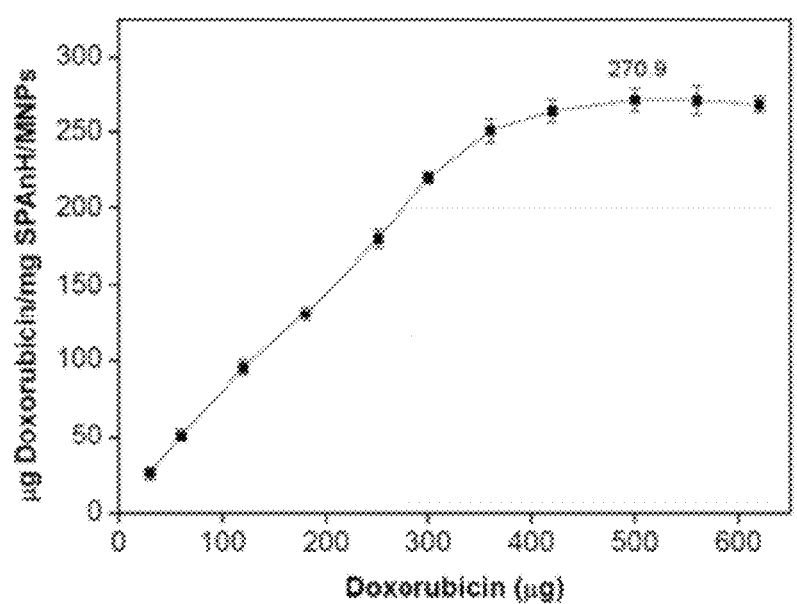
FIG. 6 is a bonding efficiency curve for bonding DOX of various concentrations onto SPAnH/MNPs magnetic nanocomposite according to the present invention.

Efficiency of Forming DOX/SPAnH/MNPs Magnetic Nanomedicine by Making Doxorubicin (DOX) of Various Concentrations to React with SPAnH/MNPs Magnetic Nanocomposite, and the Maximum Medicine Bonding Efficiency Dissolve 24 mg of EDC (1-ethyl-3-3-(dimethylaminepropyl) carbodiimide hydro chloride) and 27 mg of sulfo-NHS (N-hydroxysulfosuccinimide sodium salt) in 0.5 M MES buffer (2-Morpholinoethanesulfonic acid, pH=6.3) to form a mixed reaction solution. Next, take 0.2 mL of the mixed reaction solution to react with 0.2 mL of SPAnH/MNPs magnetic nanocomposite solution for 30 minutes, and then flush the product with the MES buffer. Then, add 30 μg, 120 μg, 360 μg, or 500 μg of Doxorubicin (DOX) medicine and perform medicine bonding reaction in temperature 20 to 25° C., to form DOX/SPAnH/MNPs magnetic nanomedicine, with its structure as shown in FIG. 9. Subsequently, flush off free DOX several times with deionized water. Then, determine the quantity of the flushed-off free DOX with HPLC (High Performance Liquid Chromatography), under the conditions of using a solution of alcohol/methanol/water (v/v/v) 15/35/50, a flow rate of 1.5 mL/min and a detecting wavelength 256 nm. Work out the quantity of DOX bonded to each mg SPAnH/MNPs magnetic nanocomposite from the quantity of the free DOX. Refer to FIG. 6, which shows that after SPAnH/MNPs magnetic nanocomposite reacts with 30 μg, 120 μg, 360 μg, or 500 μg of Doxorubicin (DOX), the amount of DOX bonded onto each mg of SPAnH/MNPs magnetic nanocomposite are 25.9 μg, 95.1 μg, 251.0 μg, or 270.9 μg, such that their medicine bonding efficiencies are 86%, 79%, 70%, 54% respectively. Therefore, it can be known that, the maximum amount of DOX that can be bonded onto each mg of SPAnH/MNPs magnetic nanocomposite.

Figure 3B:
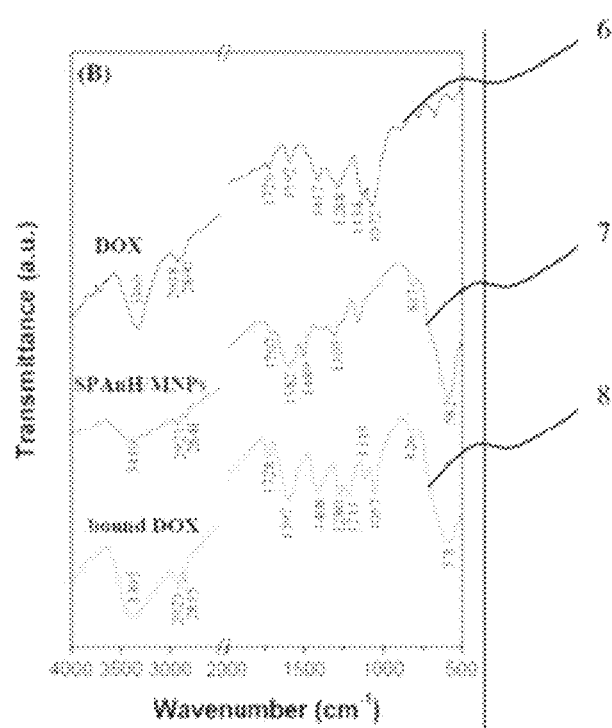
FIG. 3(B) is an infrared spectrum analysis diagram of Doxorubicin (DOX), SPAnH/MNPs magnetic nanocomposite, and DOX/SPAnH/MNPs magnetic nanomedicine detected and taken in room temperature according to the present invention.

Refer to FIG. 3B for infrared spectrum of DOX/SPAnH/MNPs magnetic nanomedicine. In this spectrum, there is an Fe—O ($vF_{e-O}$) stretching vibration appearing at 578 cm⁻¹, a saturation-symmetric stretching vibration and a saturation-asymmetric stretching vibration of C—H ($v_{C-H}$) appearing respectively at 2855 and 2923 cm$^{-1}$; C=O ($v_{C=O}$) stretching vibration of cyclopentanone, appearing at 1728 cm$^{-1}$; C—O—C ($v_{C-O-C}$) stretching vibration appearing at 1119 cm$^{-1}$; and C—O ($v_{C-O}$) stretching vibration appearing at 1057 cm$^{-1}$, such that it indicates there are indeed DOX bonded onto the SPAnH/MNPs magnetic nanocomposite.

Embodiment 5

Method of preparing Cy5/SPAnH/MNPs Magnetic Nanomedicine

Dissolve 24 mg of EDC (1-ethyl-3-3-(dimethylaminepropyl) carbodiimidehydro chloride) and 27 mg of sulfo-NHS (N-hydroxysulfosuccinimide sodium salt) in 0.5 M MES buffer (2-Morpholinoethanesulfonic acid, pH=6.3) to form a mixed reaction solution. Next, take 0.2 mL of the mixed reaction solution to react with 0.2 mL of SPAnH/MNPs magnetic nanocomposite solution for 30 minutes, and then flush the product with the MES buffer. Then, add mono-functional hydrazide cyanine 5 (Cy5) solution to perform medicine bonding reaction, and flush off free Cy5 several times with deionized water, hereby obtaining Cy5/SPAnH/MNPs magnetic nanocomposite.

Embodiment 6

Effect of EPI/SPAnH/MNPs Magnetic Nanomedicine on the Growth of Bladder Tumor Cells Cell Cultivation: Place 150 μL of a mixture liquid containing 10,000 human bladder tumor cells (MGH-U1) into each well of 96-well culture plate. Place the culture plate in a humidified incubator in a temperature of 37° C. and with 5% CO$_2$ to enable adherent growth of the cells.

Agent Addition: 24 hours later, mix separately MNPs (concentration 600 μg/mL) EPI (concentrations 2, 5, 10 μM), and EPI/SPAnH/MNPs magnetic nanomedicine (concentrations 2, 5, 10 μM) with a RPMI1640 medium to form mixed solutions. Add respectively 50 μL of the mixed solutions to well, and then place the culture plate in a humidified incubator having 5% CO$_2$ for 2, 4, 6, 10, and 27 hours.

Cell Counting: Remove RPMI1640 medium in the well and add 120 μL of an XTT reaction liquid (2,3-Bis(2-methoxy-4-nitro-5-sulfophenyl)-2H-tetrazolium-5-carboxanilide inner salt) to the wells. Use an ELISA reader (BIO-TEK, model EL 808) to measure the OD (Optical Density) values of each cell at a wavelength of 490 nm to determine the toxicity of SPAnH/MNPs magnetic nanocomposite and the cell-killing rate of EPI/SPAnH/MNPs magnetic nanomedicines to the bladder tumor cells.

Figure 7:
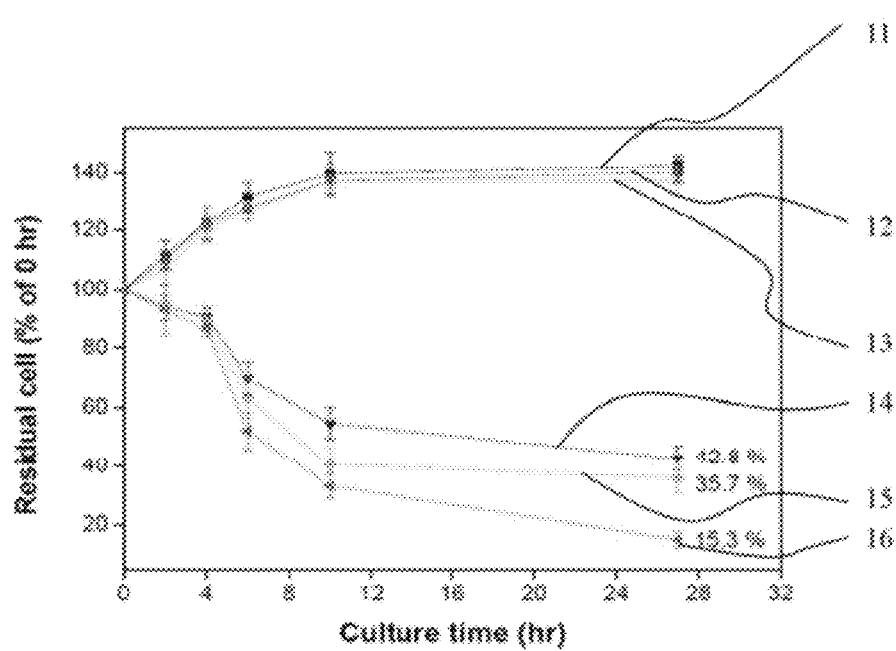
FIG. 7 is a growth suppression curve of bladder tumor cell MGH-U1 as caused by different medicines according to the present invention.

Test Results: As shown in FIG. 7, SPAnH/MNPs magnetic nanocomposites do not show any toxicity to bladder tumor cells (MGH-U1) after the bladder tumor cells have been cultivated with SPAnH/MNPs magnetic nanocomposites for 27 hours. Even when a magnetic field is applied to move SPAnH/MNPs magnetic nanocomposites to the bladder tumor cells, the bladder tumor cells are not poisoned by SPAnH/MNPs magnetic nanocomposites either. However, after EPI/SPAnH/MNPs magnetic nanomedicines of concentration of 2 μM and 5 μM are cultivated with bladder tumor cells (MGH-U1) together for 10 hours, slight bladder tumor cell growth inhibition effects start to appear, yet after 10 hours the bladder tumor cell continue to grow, and that indicates that the EPI/SPAnH/MNPs magnetic nanomedicines of such concentrations are not capable of continuously inhibiting growth of bladder tumor cells (MGH-U1). But when the concentration of EPI or EPI/SPAnH/MNPs magnetic nanomedicines is increased to 10 μM, and it is cultivated with bladder tumor cells (MGH-U1) for 27 hours, it can still continuously inhibit growth of bladder tumor cells (MGH-U1), and the cell growth inhibit efficiency are 64.3% and 57.2% respectively. Therefore, it can be estimated that, after EPI is bonded to SPAnH/MNPs magnetic nanocomposite, it can still keep 89.0% its activity. Moreover, in case that a magnetic field (800 Gauss) is applied below the cultivation plate, then the cell growth inhibit efficiency can be raised to 84.7%. It is evident that the magnetic field guides most of EPI/SPAnH/MNPs magnetic nanomedicines to concentrate to the site of bladder tumor cells, to feed more medicines to the cells, thus creating much more cell toxicity, in achieving better effect of inhibiting growth of bladder tumor cells.

Embodiment 7

Effect of DOX/SPAnH/MNPs Magnetic Nanomedicine on the Growth of Bladder Tumor Cells Cell Cultivation: Place 150 μL of a mixture liquid containing 10,000 human bladder tumor cells (MGH-U1) into each well of 96-well culture plate. Place the culture plate in a humidified incubator having 5% CO$_2$ in a temperature of 37° C. to enable adherent growth of the cells.

Agent Addition: 24 hours later, mix separately MNPs (concentration, 600 μg/mL), DOX (concentrations 2, 5, 10 μM), and DOX/SPAnH/MNPs magnetic nanomedicine with a RPMI1640 medium to form mixed solutions. Add respectively 50 μL of the mixed solutions to each well, and then place the cultivation plate in a humidified incubator having 5% CO$_2$ in a temperature of 37° C. for 2, 4, 6, 10, and 27 hours.

Cell Counting: Remove RPMI1640 medium and add 120 μL of an XTT reaction liquid (2,3-bis(2-methoxy-4-nitro-5-sulfophenyl)-2H-thtrazolium-5-carboxanilide inner salt) to the wells. Use an ELISA reader (BIO-TEK, model EL 808) to measure the OD (Optical Density) values of each cell at a wavelength of 490 nm to determine the toxicity of SPAnH/MNPs magnetic nanocomposite and the cell-killing rate of DOX/SPAnH/MNPs magnetic nanomedicines to the bladder tumor cells.

Figure 8:
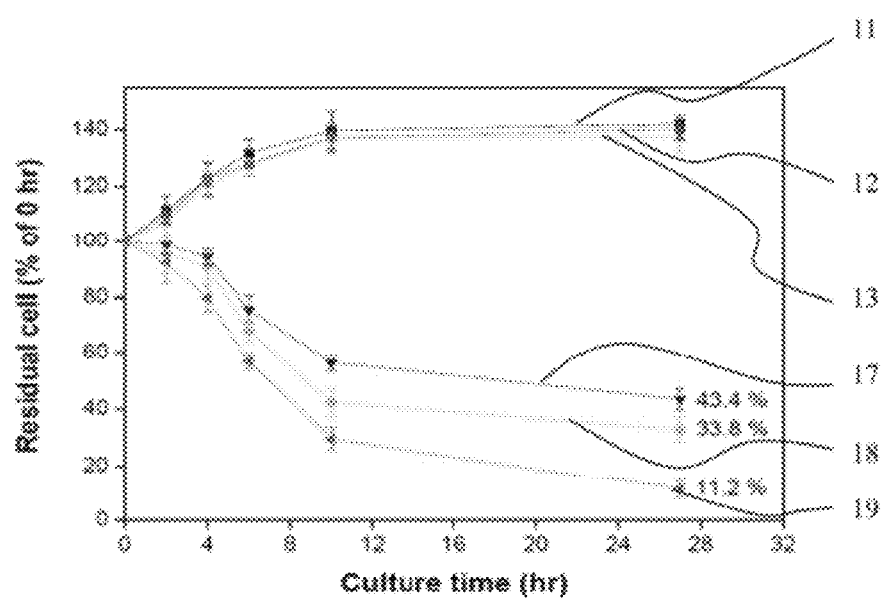
FIG. 8 is a growth suppression curve of bladder tumor cell MGH-U1 as caused by different medicines according to the present invention.

Test Results: As shown in FIG. 8, the SPAnH/MNPs magnetic nanocomposites do not show any toxicity to bladder tumor cells (MGH-U1) after the bladder tumor cells have been cultivated with SPAnH/MNPs magnetic nanocomposites for 27 hours. Even when a magnetic field is applied to move SPAnH/MNPs magnetic nanocomposites to the bladder tumor cells, the bladder tumor cells are not poisoned by SPAnH/MNPs magnetic nanocomposites. However, after DOX/SPAnH/MNPs magnetic nanomedicines of concentrations of 2 μM and 5 μM are cultivated with bladder tumor cells (MGH-U1) together for 10 hours, slight bladder tumor cell growth inhibition effects start to appear, yet after 10 hours the bladder tumor cell (MGH-U1) continue to growth, and that indicates that the DOX/SPAnH/MNPs magnetic nanomedicine of such concentrations are not capable of continuously inhibiting growth of bladder tumor cells (MGH-U1). But when the concentration of DOX or DOX/SPAnH/MNPs magnetic nanomedicines is increased to 10 μM, and it is cultivated with bladder tumor cells (MGH-U1) for 27 hours, it can still continuously inhibit growth of bladder tumor cells (MGH- U1), and the cell growth inhibit efficiency are 66.2% and 56.6% respectively. Therefore, it can be estimated that, after DOX is bonded to SPAnH/MNPs magnetic nanocomposite, it can still keep 85.5% its activity. Moreover, in case that a magnetic field (800 Gauss) is applied below the cultivation plate, then the cell growth inhibit efficiency can be raised to 88.8%. It is evident that the magnetic field guides most of DOX/SPAnH/MNPs magnetic nanomedicines to concentrate to the site of bladder tumor cells, to feed more medicines to the cells, thus creating much more cell toxicity, in achieving better effect of inhibiting growth of bladder tumor cells.

Embodiment 8

Effect of SPAnH/MNPs Magnetic Nanocomposite on the Growth of Bladder Tumor Cells Add 2 mL of a mixture liquid containing 20,000 bladder tumor cells MGH-U1 to a 3.5 cm diameter cultivation plate. Place the cultivation plate in a humidified incubator having 5% $CO_2$ in a temperature of 37° C., to enable adherent growth of the cells. Twenty-four hours later, add to the cultivation plate, 100 µL of RPMI1640 medium containing Cy5/SPAnH/MNPs magnetic nanocomposite to react for 4 hours, then flush it with 1 mL of Hanks' balance slat solution (HBSS), then add 1 mL of live/dead dye to perform dyeing of cells.

As shown in Attachment 1, the Cy5/SPAnH/MNPs magnetic nanocomposite enters the bladder tumor cell MGH-U1, but does not enter into core of cell ((C) in attachment 1), and the cell still present green fluorescent light indicating living state, that means that SPAnH/MNPs magnetic nanocomposite does not have biological toxicity (Attachment 1(B), FIG. 9B).

Embodiment 9

Effects of EPI/SPAnH/MNPs Magnetic Nanomedicines and DOX/SPAnH/MNPs Magnetic Nanomedicines on the Growth of Bladder Tumor Cell Add 2 mL of a mixture liquid containing 20,000 bladder tumor cells MGH-U1 to a 3.5 cm diameter cultivation plate. Place the cultivation plate in a humidified incubator having 5% $CO_2$ in a temperature of 37° C. to enable adherent growth of the cells. Twenty-four hours later, add to the cultivation plate, 100 µL of RPMI1640 medium containing EPI, EPI/SPAnH/MNPs magnetic nanomedicine, DOX, and DOX/SPAnH/MNPs magnetic nanomedicine to react for 4 hours, then flush it with 1 mL of Hanks' balance slat solution (HBSS).

As shown in Attachment 2, from the fluorescent microscope photos it can be known that EPI, EPI/SPAnH/MNPs magnetic nanomedicine, and DOX, DOX/SPAnH/MNPs magnetic nanomedicine do enter into the bladder tumor cell MGH-U1, and they further enter into core of cell to perform reactions required, however, the amount of EPI/SPAnH/MNPs magnetic nanomedicine and DOX/SPAnH/MNPs magnetic nanomedicine in the cell is evidently more than that of EPI and DOX, that is because EPI/SPAnH/MNPs magnetic nanomedicine and DOX/SPAnH/MNPs magnetic nanomedicine can enter into the cell in large quantity through the pinocytosis of the cell, and also they are not affected by the P-glycoprotein pumps and will not be transported out of the cell. In addition, EPI and DOX will not lose their original activities for being bonded to SPAnH/MNPs magnetic nanocomposites. Furthermore, EPI/SPAnH/MNPs magnetic nanomedicine and DOX/SPAnH/MNPs magnetic nanomedicine can be guided by an outside magnetic field to concentrate into a specific area, in achieving increased local medicine concentrations.

Embodiment 10

Cell Slice Observation of Bladder Tumor Cell after being Acted on by SPAnH/MNPs Magnetic Nanocomposite and EPI/SPAnH/MNPs Magnetic Nanomedicine Place SPAnH/MNPs magnetic nanocomposite and EPI/SPAnH/MNPs magnetic nanomedicine together with bladder tumor cell MGH-U1 to cultivate for 2 hours, then take out the bladder tumor cell MGH-U1 and cut it into thin slices, subsequently use Transmission Electronic Microscope (TEM) to observe the diameters of SPAnH/MNPs magnetic nanocomposite and EPI/SPAnH/MNPs magnetic nanomedicine, and their distributions in the cell, and compare that with the observation results of MNPs obtained through using TEM. Furthermore, observe and analyze the crystallographic structure of the cell slice utilizing electronic diffraction patterns.

Figure 1B:
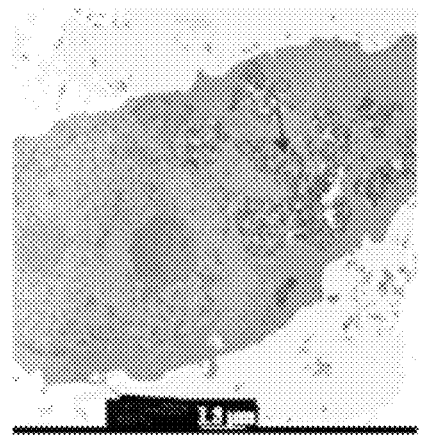
FIG. 1(B) is a transmission electronic microscopic photo of bladder tumor cell MGH-U1 cultivated together with magnetic nanocomposite of magnetic nanoparticles of a shell encapsulated with carboxylated polyaniline (SPAnH) (magnified 3000 times) according to the present invention.
Figure 1C:
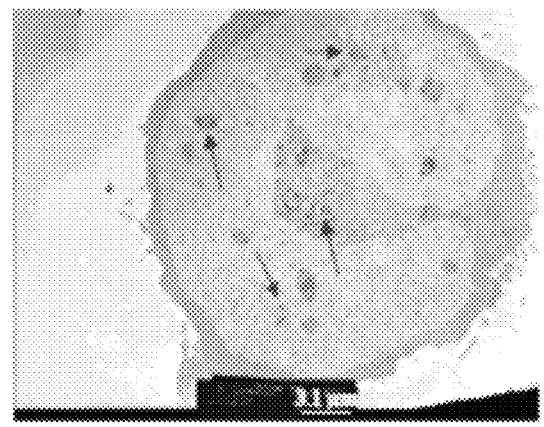
FIG. 1(C) is a transmission electronic microscopic photo of bladder tumor cell MGH-U1 cultivated together with EPI/SPAnH/MNPs magnetic nanocomposite (magnified 5000 times) according to the present invention.

Refer to FIGS. 1(A) and 1(C), wherein it shows that the particle diameter of SPAnH/MNPs magnetic nanocomposite is about 17 nm, and its crystallographic planes are (400), (311), (422), (220), and (440) respectively. It can prove that MNPs and SPAnH/MNPs magnetic nanocomposite contain $Fe_3O_4$ crystal according to the Specifications of JCPDS (Joint Committee on Powder Diffraction Standards).

Refer to FIG. 1(B), wherein it shows placing SPAnH/MNPs magnetic nanocomposite into cultivation plate containing bladder tumor cell MGH-U1, and after 2 hours of cultivation, it is found that SPAnH/MNPs magnetic nanocomposite may enter into the bladder tumor cell MGH-U1 through endocytosis, however, it can not enter into core of the cell, thus it does not have biological toxicity.

Figure 1D:
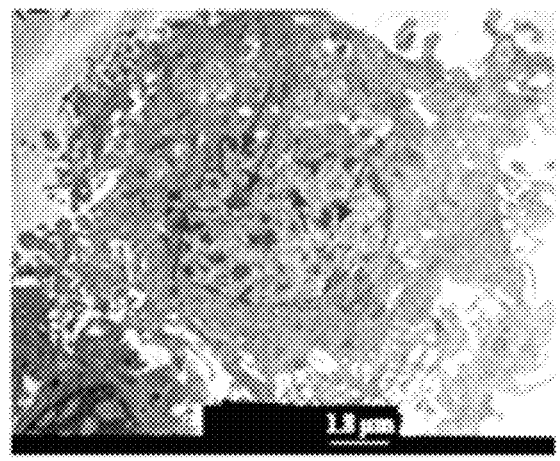
FIG. 1(D) is a transmission electronic microscopic photo of bladder tumor cell MGH-U1 cultivated together with DOX/SPAnH/MNPs magnetic nanocomposite (magnified 5000 times) according to the present invention.
Figure 1E:
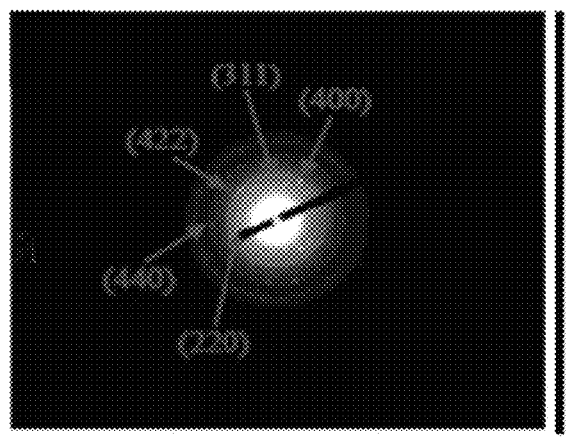
FIG. 1(E) transmission electronic microscopic photos of FIG. 1(A) to FIG. 1(D)

Refer to FIGS. 1(C) and 1(D), wherein they show that in case that EPI/SPAnH/MNPs magnetic nanomedicine is added to a cultivation plate containing bladder tumor cell MGH-U1, and after 2 hours of cultivation, it is found that EPI/SPAnH/MNPs magnetic nanomedicine may enter into bladder tumor cell MGH-U1 through pinocytosis, and it can enter further into core of cell in achieving the effect of cell-killing. From the electronic diffraction pattern of EPI/SPAnH/MNPs magnetic nanomedicine, it can be known that, the crystallographic planes of the black particles (shown by red arrow) in the cell are (400), (311), (422), (220), and (440) respectively, which are identical to those of MNPs. It can prove that the black particles in the cell are indeed the SPAnH/MNPs magnetic nanocomposite, hereby confirming that SPAnH/MNPs magnetic nanocomposite indeed can bring EPI into cell in achieving cell-killing effect.

Summing up the above and in conclusion, the present invention bonds Epirubicin (EPI), Doxorubicin (DOX) or derivatives thereof used for treating malignant tumor, to the surface of a magnetic nanocomposite to form magnetic nanomedicine having particle diameter of 20-50 nm. The magnetic nanomedicine of the present invention is free of toxic chemicals, such as surfactants, dispersing agents and crosslinking agents, and has higher thermal stability and water-solubility and lower biological rejection. Furthermore, the magnetic nanocomposite of the present invention can be guided by an external magnetic field to gather around the position of tumor cell distribution, to raise local medicine concentration in achieving concentrated therapy.

The above detailed description of the preferred embodiment is intended to describe more clearly the characteristics and spirit of the present invention. However, the preferred embodiments disclosed above are not intended to be any restrictions to the scope of the present invention. Conversely, its purpose is to include the various changes and equivalent arrangements which are within the scope of the appended claims.

What is claimed is:

1. A magnetic nanomedicine for tumor suppression and therapy, comprising:
   a core, made of magnetic particles of diameter less than 10 nm;
   a shell, encapsulating said core and is made of carboxylated polyaniline(SPAnH); and
   a tumor suppression medicine, covalently bonded on said shell,
wherein said magnetic particles forming said core are selected from a group consisting of: $Fe_3O_4$, $Fe_2O_3$, and $Ni_3$, and
wherein said shell is composed of carboxylated polyaniline (SPAnH), having the following formula:

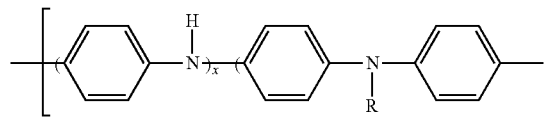

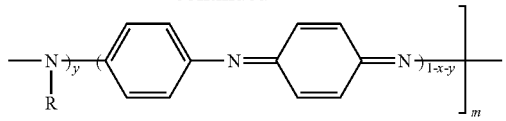

wherein, R is selected from a group consisting of the following functional groups:
   H, —$COR_1COO^-$, —$COR_1COOH$, —$COR_1COOLi$, —$COR_1COONa$, —$COR_1COOK$, —$COR_1COONH_4^+$, $COR_1CONH_2$, —$R_1COO^-$, —$R_1COOH$, —$R_1COOLi$, —$R_1COONa$, —$R_1COOK$, —$R_1COONH_4^+$, and —$R_1CONH_2$; and $R_1$ is selected from a group of compounds consisting of: alkane group and vinyl group composed of 2 to 4 carbon atoms.

2. The magnetic nanomedicine for tumor suppression and therapy as claimed in claim 1, wherein particle diameter of said magnetic nano-medicine is between 25 to 50 nm.

3. The magnetic nanomedicine for tumor suppression and therapy as claimed in claim 1, wherein said tumor suppression medicine is covalently bonded on said shell in a temperature between 20° C. to 25° C.

4. The magnetic nanomedicine for tumor suppression and therapy as claimed in claim 1, wherein said tumor suppression medicine is Epirubicin (EPI) and derivative thereof.

5. The magnetic nanomedicine for tumor suppression and therapy as claimed in claim 1, wherein said tumor suppression medicine is Doxorubicin (DOX) and derivative thereof.

* * * * *